United States Patent [19]

von Zeppelin

[11] 4,433,689

[45] Feb. 28, 1984

[54] SURGICAL CLAMP FOR VESSELS

[76] Inventor: Dieter von Zeppelin, Wittelsbacher Str. 20, D-8000 Munchen 5, Fed. Rep. of Germany

[21] Appl. No.: 237,979

[22] Filed: Feb. 25, 1981

[30] Foreign Application Priority Data

Mar. 3, 1980 [DE] Fed. Rep. of Germany ....... 3008122

[51] Int. Cl.³ .............................................. A61B 17/12
[52] U.S. Cl. ..................................... 128/346; 128/325
[58] Field of Search ....................... 128/346, 321–322, 128/325, 327; 24/137 R, 67.5

[56] References Cited

U.S. PATENT DOCUMENTS

| 2,493,503 | 1/1950 | Renne | 24/137 R |
|---|---|---|---|
| 2,733,716 | 2/1956 | Roberts | 128/321 |
| 3,326,217 | 6/1967 | Kerr | 128/325 |
| 3,349,771 | 10/1967 | Baer | 128/346 X |
| 3,579,751 | 5/1971 | Jonckheere | 128/346 X |
| 3,598,125 | 8/1971 | Cogley | 128/346 |
| 3,636,954 | 1/1952 | Weston | 128/321 |
| 3,676,902 | 7/1972 | Pearson | 24/67.5 X |
| 3,777,760 | 12/1973 | Essner | 128/321 X |
| 4,192,315 | 3/1980 | Hilzinger et al. | 128/346 |
| 4,274,415 | 6/1981 | Kanamoto et al. | 128/321 |

Primary Examiner—Lee S. Cohen
Assistant Examiner—Angela D. Sykes
Attorney, Agent, or Firm—Burns, Doane, Swecker & Mathis

[57] ABSTRACT

A surgical clamp for the clamping of small blood vessels is formed of a piece of spring material and has two jaw sections urged against each other by the spring action of the material. The jaw sections include opposing parts which progressively increase in resiliency in opposite directions so that the total clamping force is essentially constant along the length of the jaw.

2 Claims, 3 Drawing Figures

SURGICAL CLAMP FOR VESSELS

BACKGROUND AND OBJECTS OF THE INVENTION

The invention concerns a surgical clamp for vessels, the clamp being made of a spring material, wherein two jaw sections are urged against each other by the spring action of the material.

Clamps of this type are used for example in the microsurgery of vessels and in neurosurgery to clamp off very small vessels temporarily or permanently. However, other applications are conceivable.

Very small clamps for vessels are known, wherein the jaws in the open condition have the approximate configuration of a V and are urged against each other in the closed state by the spring action of the material. During the clamping of a vessel therein the part of the vessel located inside the clamp is pressured to a greater degree than the part to the outside, i.e., there is a differential distribution of the clamping force over the length of the jaw, wherein the clamping force on the inside may be two to three times the magnitude of the force on the outside.

It is the object of the invention to provide a surgical clamp for vessels of the above-described type, whereby a uniform clamping force may be obtained over the entire length of the jaw.

SUMMARY OF THE INVENTION

This is attained according to the invention in that one of the jaw sections has a part that is turned back at the free end of the jaw part. The turned back part is approximately parallel to the other jaw part.

This results in the fact that not only are the parts of the clamping jaw cooperating with each other approximately parallel to each other, but the end of said cooperating parts of the jaw are pointing with their highest elasticity in different directions, so that the clamping is extensively constant over the entire length of the jaw. By means of a clamp for vessels of this type, a vessel may be clamped or sealed simply, rapidly, and safely, while the vessel itself is held very gently by virtue of the uniform distribution of pressure. Furthermore, the clamp may be made with very small dimensions, so that it may be applied when very little space is available, as is often the case in microsurgery.

Conveniently, the clamp consists of a single piece of stainless material, whereby soldered or welded joints potentially inducing corrosion phenomena and subsequent failures, are avoided.

THE DRAWINGS

The invention shall be explained hereinbelow by means of examples of embodiments and with the aid of the drawing attached hereto. In the drawing.

DETAILED DESCRIPTION OF PREFERRED EMBODIMENTS OF THE INVENTION

Figure 3:
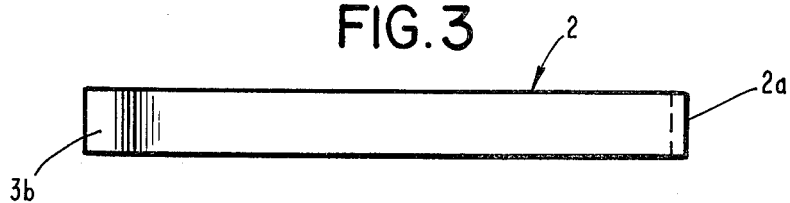
FIG. 3 is a side view of the clamp of FIG. 1.
Figure 1:
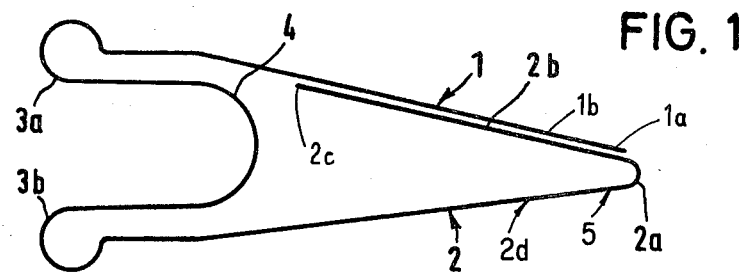
FIG. 1 shows an example of embodiment of the clamp for vessels according to the invention in top view, wherein the clamp is equipped with two handles for manual actuation.

FIG. 1 shows an example of an embodiment of a clamp for vessels. The clamp is made of a single piece or strip of resilient material, wherein the sections of the jaw itself are designated by numerals 1 and 2. The two jaw sections 1 and 2 are provided at their rear or base ends with special handles 3a and 3b, connected with each other by a turned back arch-shaped reversal 4, having its convexity pointing in the forward direction. The first and second jaw sections 1 and 2 are cantilevered at the base and are urged toward each other by the inherent resiliency of the material. The vessel may enter via the free ends 1a, 2b of the jaw sections as the latter separate. The jaw sections include vessel-engaging parts 1b, 2a having free ends 1a, 2c at opposite ends. More specifically, the first jaw section 1 comprises a first part 1b of the strip which extends forwardly to a forward end 5 of the jaw and terminates there to form the free end 1a of the part 1b. The second section 2 of the jaw includes a second part 2d of the strip which extends forwardly to the forward end 5 and reverses direction there to define a third part 2b of the strip which extends rearwardly adjacent the part 1b of the jaw. The third part 2b terminates at a location rearwardly of the front end 5 to form the free end 2c of the part 2b. That is, the part 2b of the section 2 of the jaw is turned back at the free end 2a of that jaw section and extends back in a direction approximately parallel to the part 1b of the jaw. Thus, the free end 1a of the part 1b corresponds to the free end of its jaw section 1, while the free end 2c of the part 2b is located rearwardly of the free end 2a of its jaw section 2. The second part 2b is longer than the first part 1b. Accordingly, the part 2b itself is cantilevered at the free end 2a of the jaw section 2 whereby the parts 1b and 2b may be considered cantilevered in opposite directions. In any event, it will be appreciated that the parts 1b, 2b become progressively more resilient toward their free ends 1a, 2c since those free ends have the highest degree of resiliency of the parts 1b, 2b. Thus, the part 1b becomes more resilient (less stiff) in the forward direction and the part 2b becomes more resilient in the rearward direction. Hence, the combined resiliency of the jaw itself becomes relatively balanced through its length.

The clamp is preferably formed of a stainless material, such as stainless steel for example.

Figure 2:
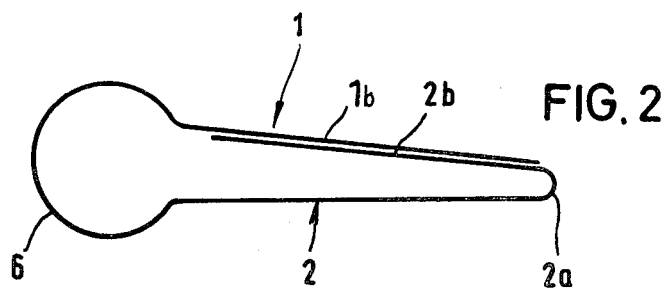
FIG. 2 is a modified example of embodiment, wherein the clamp is actuated by means of a special tool.

FIG. 2 shows an embodiment of the calmp for vessels that is overall more compact and shorter and which differs from the clamp of FIG. 1 only in an arch-shaped reversal 6, pointing in the rearward direction. This embodiment results in a substantially shorter longitudinal dimension of the clamp, whereby the latter may be used even in highly restricted space conditions. The actuation of this clamp in actual practice is effected by means of a special tool, which is inserted in the reversed part 6 and which moves the parts 1 and 2 of the jaw away from each other by expanding said reversed part 6.

As noted earlier, in all of the known conventional clamps the clamping force varies in the longitudinal direction of the jaw of the clamp, whereby a vessel that could be sealed off with a given force must necessarily be clamped with a force that is several times larger. As the surgical clamp according to the invention has a uniform clamping force over the entire length of the jaw, such differences in pressure are avoided and clamping that is truly gentle is obtained for the first time.

By varying the width, the thickness and/or the length of the material of the clamp, the reversed part, etc., the clamping force of the jaw may be varied to suit a particular application.

Although the invention has been described in connection with preferred embodiments thereof, it will be appreciated by those skilled in the art that additions, modifications, substitutions, and deletions may be made, without departing from the spirit and scope of the invention as defined in the appended claims.

What is claimed is:

1. A surgical clamp for vessels, said clamp comprising a single strip of resilient spring material formed to have an arched section at a rear end thereof and first and second jaw-forming sections extending forwardly of said arched section, said first jaw-forming section comprising a first portion of said strip which extends forwardly to a forward end of said first jaw-forming section and terminates at such forward end, said second jaw-forming section comprising a second portion of said strip which extends forwardly to a forward end of said second jaw-forming section and then reverses direction to define a third portion of said strip extending rearwardly adjacent said first portion, said third portion terminating at a location rearwardly of said forward end of said first jaw-forming section, said second portion being longer than said first portion, the first and third portions being resiliently separable to receive therebetween a vessel to be clamped whereby a substantially uniform clamping force is obtained over the entire coincident lengths of the first and third portions.

2. A surgical clamp according to claim 1, wherein said arched section defines a convexity which faces forwardly, said arched section having first and second ends which are joined to rear ends of said first and second portions respectively, to form manual gripping handles.

* * * * *